(12) United States Patent
Vizethum et al.

(10) Patent No.: US 8,486,123 B2
(45) Date of Patent: Jul. 16, 2013

(54) MICRO-ORGANISM-REDUCING DEVICE

(75) Inventors: Freimut Vizethum, Mannheim (DE); Reinhold Schuetze, Attnang-Puchheim (AT)

(73) Assignee: bredent medical GmbH & Co., KG, Baar (CH)

( * ) Notice: Subject to any disclaimer, the term of this patent is extended or adjusted under 35 U.S.C. 154(b) by 1624 days.

(21) Appl. No.: 10/558,453

(22) PCT Filed: May 27, 2004

(86) PCT No.: PCT/EP2004/005719
§ 371 (c)(1),
(2), (4) Date: Dec. 22, 2006

(87) PCT Pub. No.: WO2004/105874
PCT Pub. Date: Dec. 9, 2004

(65) Prior Publication Data
US 2008/0051856 A1    Feb. 28, 2008

(30) Foreign Application Priority Data

May 28, 2003   (DE) ................................. 103 24 644
Oct. 23, 2003   (DE) ................................. 103 49 710

(51) Int. Cl.
*A61N 5/06*   (2006.01)
(52) U.S. Cl.
USPC ...................... 607/88; 606/2; 606/13; 607/89
(58) Field of Classification Search
None
See application file for complete search history.

(56) References Cited

U.S. PATENT DOCUMENTS

| 4,754,328 | A | * | 6/1988 | Barath et al. ................... 348/67 |
| 4,785,805 | A | | 11/1988 | Joffe et al. |
| 5,029,581 | A | | 7/1991 | Kaga et al. |
| 5,116,329 | A | * | 5/1992 | Vannus et al. ................. 606/11 |
| 5,242,439 | A | | 9/1993 | Larsen et al. |
| 5,454,794 | A | | 10/1995 | Narciso et al. |
| 6,129,721 | A | * | 10/2000 | Kataoka et al. .................. 606/2 |
| 6,443,978 | B1 | * | 9/2002 | Zharov ............................ 607/91 |
| 2002/0177099 | A1 | * | 11/2002 | Cao ................................ 433/29 |

FOREIGN PATENT DOCUMENTS

| DE | 39 18 965 | 7/1990 |
| DE | 100 49 999 | 4/2002 |
| EP | 0 438 241 | 7/1991 |
| EP | 0 637 976 | 2/1995 |
| EP | 0 761 257 | 3/1997 |
| JP | 4-136243 | 12/1992 |
| JP | 5-245156 | 9/1993 |
| JP | 11-155638 | 6/1999 |
| JP | 11-244295 | 9/1999 |

(Continued)

*Primary Examiner* — Bill Thomson
*Assistant Examiner* — Lynsey Crandall
(74) *Attorney, Agent, or Firm* — Jordan and Hamburg LLP

(57) ABSTRACT

The invention relates to a micro-organism reducing device, comprising a radiation device which is provided with a light source, a photosensitive substance which treats the area to be treated and is irradiated by said light source. The aim of said invention is to configure said device in such a way that it is possible to carry out an efficient and controllable treatment by means of operationally low-cost and easily handling apparatus. For this purpose, the inventive device comprises at least one applicator provided with a fiber-optic waveguide. In addition, said applicator and radiation device respectively comprise corresponding liaison bodies contacting one of them in such a way that the light from the light source is emitted towards the treated area by means of the fiber-optic waveguide.

15 Claims, 23 Drawing Sheets

FOREIGN PATENT DOCUMENTS

| | | |
|---|---|---|
| JP | 2001-017556 | 1/2001 |
| JP | 2002-507135 | 3/2002 |
| JP | 2002-517295 | 6/2002 |
| WO | WO-95/05214 | 2/1995 |
| WO | WO-99/00062 | 1/1999 |
| WO | WO-99/64109 | 12/1999 |
| WO | WO-01/87416 | 11/2001 |
| WO | WO-02/13712 | 2/2002 |

* cited by examiner

FIG. 1

Pocket probe – perpendicular

Output power 15.5 mW

| Diameter | 0.1 mm | 0.2 mm |
|---|---|---|
| Distance from light source to glass surface | Measured power on measuring surface [mW] | Measured power on measuring surface [mW] |
| 1% methylene blue solution | | |
| 0 mm | 0.39 | 0 |
| 5 mm | 0.38 | 0 |
| 10 mm | 0.35 | 0 |
| 15 mm | 0.34 | 0 |
| 20 mm | 0.33 | 0 |
| 30 mm | 0.29 | 0 |
| 0.1% methylene blue solution | | |
| 0 mm | 8.3 | 3.3 |
| 5 mm | 8.1 | 3.3 |
| 10 mm | 8 | 3.3 |
| 15 mm | 7.7 | 3.3 |
| 20 mm | 7.1 | 3.1 |
| 30 mm | 5.9 | 2.6 |

FIG. 19
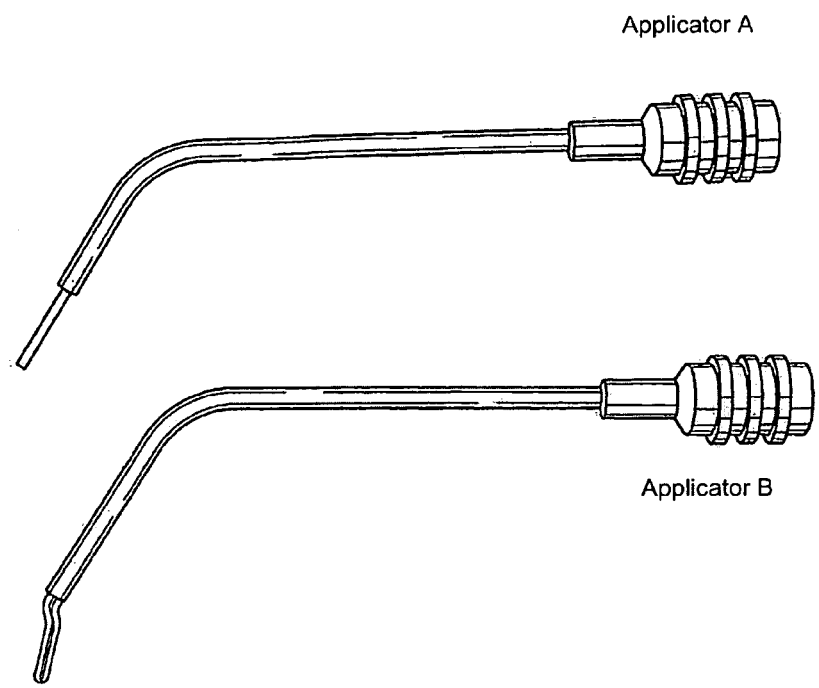
Applicator A
Applicator B
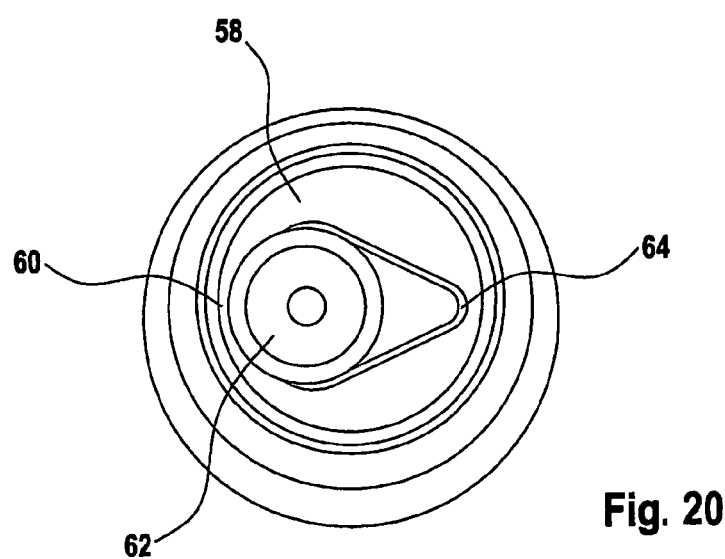
Fig. 20

MICRO-ORGANISM-REDUCING DEVICE

BACKGROUND OF THE INVENTION

The invention relates to an arrangement for reducing microorganisms. The invention furthermore relates to the use of such an arrangement for therapy, in particular in the mouth, jaw, and facial area.

Known from WO 01/87416 A1 is such an arrangement and a method for reducing or destroying microorganisms, such as bacteria, using a light-activatable substance and photodynamic therapy (PDT). Using the light-activatable substance, in particular a stain, the microorganisms are sensitized and/or stained, and they are killed using irradiation with light of an appropriate wavelength and energy density as a result of the selective action and/or staining. The principle of action of PDT is based on the physical effect of energy transmission to the light-activatable substance, which is also called a photosensitizer. From there, the energy for reactions can be made available on the cell membrane. The energy produced by means of a radiation device, especially a laser device, is thus concentrated on the microorganisms and the equilibrium of reactions that also occur in the non-irradiated "normal" milieu are shifted and as a consequence the microorganisms are destroyed.

Furthermore known from EP 0 637 976 B1 is the use of a light-sensitizing substance or compound or photosensitizer (PS) during production of a medication for use during disinfection or sterilization of tissues in the oral cavity or a wound or lesion in the oral cavity by destroying microbes in a periodontal pocket that are associated with an illness, in the region between the tooth and the gum. The tissue, wound, or lesion is contacted with the photosensitizer, the microbes associated with the illness absorbing the photosensitizer. The tissue, wound, or lesion is irradiated with laser light at a wavelength absorbed by the photosensitizer. The reduction in germs in this combined stain and laser treatment is described for various germs and photosensitzers in the form of solutions with, among other things, methylene blue and toluidine blue in various fairly low concentrations, specifically from 0.01 to 0.00125% (weight per volume), whereby furthermore the effect of the energy density applied is indicated. HeNe lasers with a wavelength of 634 nm and an output of 7.3 mW and GaAs lasers with a wavelength of 660 nm and an output of 11 mW are used as light sources.

BRIEF SUMMARY OF THE INVENTION

Starting at this point, the underlying object of the invention is to embody the arrangement such that effective and controllable therapy is attained with an apparatus that is not very complex and with simple handling. The therapy for local, superficial infections, especially in the mouth, jaw, and facial area, should not be complex and should be highly functional. Moreover, the most homogeneous possible irradiation of the area to undergo therapy, in particular the surface of the oral mucosa, should be attained. With respect to the great distribution and great frequency of infections, especially in the area of the mouth, jaw, and face, including dentogenic infections, the problems that have existed in the past should be avoided or at least reduced.

Using a simple structure and simple handling, the inventive arrangement facilitates functional and practical application of the therapy by means of a light-activatable substance and a radiation device. The light-activatable substance is prepared in solution in a high concentration, usefully filled in a syringe sterilized and ready to use. Advantageously, the concentration of the photosensitizer is provided in a solvent such as an aqueous solution or alcohol or ethanol, with a high value. The concentration, specifically weight per volume, is advantageously greater than 0.1%, usefully greater than 0.5%, whereby the upper limit is advantageously 10%, usefully 5%, especially 3%. A concentration of at least approximately 1% has proved to be particularly suitable. The radiation device, which is in particular embodied as a laser device, is combined with an application system, whereby applicators can preferably be detachably connected to the radiation device. The applicators are advantageously single-use optics by means of which it is possible to irradiate the area to undergo therapy in a targeted and precise manner. The applicators are used only once for treatment so that in particular hygiene requirements are met and undesired transmission of microorganisms is safely avoided without complex measures for any subsequent or repeated sterilization. The applicators contain light conductors, in particular optical fibers, and enable without any problem intraoral light distribution and/or irradiation and can be embodied as pocket probes or surface probes. The radiation device and the at least one applicator are preferably embodied such that the light from the light source can be coupled directly into the light conductor. In one preferred embodiment of the invention, a light conductor or an optical fiber with a high numerical aperture is used, whereby the numerical aperture is preferably greater than 0.5, in particular greater than 0.7. Because of this, there are low losses when the light is coupled into the applicator or light conductor and at the same time it is assured that the light beam exiting the applicator or light conductor opens up.

In one preferred embodiment of the invention, a blocking device is combined with the radiation device such that light cannot exit from the radiation device unless the applicator and/or light conductor is connected. As long as the applicator is not properly connected to the radiation device, the blocking device prevents light from exiting directly out of the radiation device. In one preferred embodiment, the radiation device, in particular its head part, contains a preferably central bore into which the light conductor end of the applicator is inserted and fixed. The blocking device is especially arranged in the beam path of the light from the light source and in the free end and/or in the free end face of the light conductor end. In accordance with the invention, the blocking device is actuated when the applicator is connected and/or when the light conductor end is inserted into the aforesaid bore, such that the beam path is uncovered, in particular by means of the light conductor end. The aforesaid bore and/or the inserted light conductor end are arranged and/or aligned with respect to the light source such that the light from the light source falls on the free end face of the light conductor end, where necessary focused by means of an optical system. The applicators contain a connecting or plug-in apparatus, in particular in the form of a Luer plug, for being received on a head or head part of the radiation device. Furthermore, the applicators are embodied in an advantageous manner at least partially curved such that targeted irradiation of the areas to undergo therapy, in particular in the oral cavity, is facilitated. Furthermore, the applicators are preferably embodied at least partially flexible so that undesired injuries are avoided.

In one preferred embodiment, the light conductor has a defined geometry of the light exit area such that the light exit is matched to the shape of the sites to be irradiated in the area to undergo therapy, whereby either a two-dimensional or physical three-dimensional radiation area is produced. Furthermore, the applicator and/or the light conductor has at its tip a spacer with which an active circle of the exiting light is indicated and/or the correct or prescribed irradiation distance is established. In accordance with another embodiment, the light conductor geometry is such that penetration into narrow cavities and/or pockets of tissue with complex shapes is enabled and/or these can be opened gently. Advantageously, the light conductor has a conical tip, specifically usefully with an angle of 1.5 to 4° to the perpendicular. In addition, it has proved particularly advantageous to provide the light conductor in the area of its tip with a light exit surface having a prescribed microstructure ranging from 10 µm to 200 µm. The tip of the light conductor preferably has a micro-roughness with an Ra value ranging from 10 to 40 µm, preferably 20 to 30 µm. Moreover, the connector body of the applicator is embodied as a plug-in and/or screw-in connector with an integrated stop, thus ensuring defined positioning in the axial direction of the light conductor inserted into the radiation device with respect to the light source.

For the inventive use of the arrangement, the light-activatable substance that preferably contains stain is first applied in a high concentration to the area to undergo therapy and then rinsing is performed with a medium, in particular water and/or with the most alkaline possible pH. Thereafter, the irradiation by means of the light from the radiation device is performed, whereby in a preferred manner optimized cell damage occurs. It has proved particularly effective to first apply the light-activatable substance in a high concentration to the area to undergo therapy and subsequently to rinse with a medium, in particular water, and/or with oxygen partial pressure as high as possible, and finally to perform the irradiation by means of the light from the aforesaid light source, whereby optimized cell damage preferably occurs. Furthermore, it has proved particularly useful that after the light-activatable substance is applied in a high concentration to the area to undergo therapy and furthermore prior to the irradiation by means of the light from the light source, the quantity of light-active substance is reduced, specifically in particular by wiping and/or dabbing and/or suctioning and/or blowing air.

The structure of the arrangement and its inventive use are described in detail in the following. The arrangement contains:

1. Light-activatable substance:

The light-activatable substance present in solution, for instance methylene blue, which preferably contains a stain and is called a photosensitizer, is preferably added to a syringe and sterilized and ready for use. In particular a 26-g cannula is provided for the application to the area to undergo therapy, and it has in particular an exterior diameter of 0.45 mm, a length of 25 to 40 mm, and in particular is embodied angled at 35 to 40 degrees and elastic.

2. Radiation device with light source, in particular laser device or therapeutic laser, preferably in the following embodiments:

a. With optical system, in particular lens packet, and preferably with a threaded connector to the light conductor coupling.

b. With direct beam coupling without lens packet, with clear space in front of the diode so that without attached light conductor only a little light escapes diffuse from the access provided for coupling the light conductor. The arrangement is furthermore preferably such that when using a diode with monitoring the back-scattered light regulates the diode.

The radiation device preferably contains a blocking device, by means of which light is prevented from exiting as long as an applicator is not connected to the radiation device.

3. Application system

Single-use optics or applicators that in particular are each used only once and preferably have a light conductor and plastic covering. These are preferably flexible and/or sterilized and/or ready to use and/or compatible with both of the aforesaid radiation devices. Glass or plastic is provided as the material for the light conductor(s) in particular with a numerical aperture preferably greater than 0.5 µm in order to couple as much light as possible and furthermore to emit the light in a large area. Due to the detachable connection between the radiation device and the applicators, it is particularly important that the applicator in the framework of the invention is used only once and thereafter is disposed of as a comparatively simply constructed and cost-effective component and as a "disposable product".

Two embodiments of the applicators are usefully provided:

a. Pocket probe with conical emitting area in particular for irradiating the periodontal pocket. In one step the pocket is opened, tissue is pushed to one side, and the area is irradiated with radiation to the front and in a circle. The surface is roughened so that the radiation of the light is diffuse (for instance sanded with sandpaper 100).

b. Surface probe, preferably with spacer for irradiating superficial sites, i. the length of which marks the correct distance to the tissue, ii. the angle of which marks the area in which the therapeutically required light output is to be applied, whereby overlapping irradiation of an area is reduced.

4. Furthermore, in one preferred further development a therapy controller and/or a program for the PC and/or an independent display and control unit. These provide control and orientation for the operator during the therapy. This permits above all selection of the size of the surface to be irradiated or the number of teeth and in particular displays:

a. the time the photosensitizer takes effect, b. the time for rinsing the site, c. the time for irradiating each $cm^2$ or tooth with an acoustic signal for the end of the irradiation for each tooth or $cm^2$, d. the end of the treatment.

The components of the arrangement are explained in the following:

The energy source or light source of the radiation device is embodied such that there is sufficiently high penetration of the light in the tissue in the relevant wavelength range since long-wave radiation penetrates deeper into the tissue than short-wave radiation. Sufficiently deep penetration into the tissue with light occurs in the area of the absorption maximum of the light-activatable substance, for instance methylene blue (664 nm in NaCl or 655 nm in 96% ethanol). In the so-called optical window between 600-900 nm, the light is very slightly absorbed by chromophores such as hemoglobin or melanin.

Above all laser systems are suitable as energy or light sources. The laser (light amplification by stimulated emission of radiation) is a light source that can emit monochromatic, coherent, and collimated light at a high power. Coherent light includes temporal and spatial coherence in the wave trains.

Essentially photochemical processes are effective in the range of the inventively provided low-power and low energy densities (0.1-100 mW/cm2). In these cases, the absorption of light does not primarily lead to the tissue heating up. These effects produced in biological materials using a thermal laser applications are called "laser-induced biostimulation". Such lasers are used as the light source for the photodynamic therapy (PDT) using the photosensitizer. Photothermally induced effects can also occur with these lasers when using higher power density or higher energy density.

In diode lasers, semiconductor crystals are used as the active medium and when excited emit coherent radiation in the VIS or IR range. In these lasers, photons are produced directly using electrical current.

In connection with the photosensitizer that is preferably used, a special diode laser is used for the radiation device, hereinafter referred to as the HELBO TheraLite. The HELBO TheraLite diode laser is suitable in particular for methylene blue.

This laser system is characterized by the following properties:

| Light source | Diode |
| Wavelength | 660 nm (+5) |
| Power | Max. 100 mW |
| Mode | Cw or continuous |
| Light output power | >40 mW < 50 mW |
| Cooling system | Air |
| Energy supply | Battery or accumulator |

The application system inventively enables the transmission of the light or laser radiation. The application system provides the desired beam geometry at the site of application and enables simple handling of the laser radiation for therapy. The optical fiber is part of the application system.

One of the goals of effective and controllable therapy in the oral cavity is attaining the most homogeneous possible irradiation of the surface of the oral mucosa. However, the oral cavity is characterized by complex geometry and by the presence of very differently absorbing structures such as bones, teeth, and mucosa that clearly deviate from plane geometry. This is assured with the inventive applicators.

Optical fiber systems can conduct the required energy even into sites that are difficult to access such as in the oral cavity. For coupling into an optical fiber, the primary beam from the laser in the radiation device is focused on the fiber end either directly or through a lens packet. The numerical aperture of the fiber determines the coupling angle such that the radiation largely enters the light conductor.

The beam divergence of the optical fiber is also determined by the type of coupling into the fiber head and of the radiation device also by the numerical aperture (sine of the aperture angle) of the fiber itself. A higher divergence enables a wider transmission angle.

When fibers having a steep drop in energy, or having widely fluctuating light distribution over the irradiated surface, are used, the irradiation field is frequently irradiated in an overlapping manner.

In comparison to the bare fiber, the preferably provided microlens fiber has the most homogeneous irradiation profile. With an optimized microlens fiber, a power distribution with homogeneity of approximately 96% can be obtained over the entire irradiated surface. Overlapping the irradiation fields is not necessary when using a microlens fiber, so that it is possible to cover the infected area in a highly efficient manner and there are no unnecessary areas of overlap.

The application mode (extraoral or intraoral) is a function of the focus size, which is selected according to the findings.

One preferred alternative is provided by inventive fibers with a very high a numerical aperture with which uniformly irradiated sites can also be produced.

A numerical aperture of at least 0.5, preferably 0.7 or higher, is inventively provided in order to avoid complex grinding of fiber tips and to be able to maintain a clinically reasonable distance of 0.5 to 1 cm for the irradiation of intraoral areas.

In particular the following application system with the applicators, which are embodied as a pocket probe and/or a surface probe, is used in the framework of the invention. These applicators contain plastic light conductors that are embedded in a covering, a coupling surface with a connector to the radiation device, in particular a laser device, and a specifically ground radiation area and/or a radiation area having a microstructure.

The invention is described in greater detail in the following using the special exemplary embodiments depicted in the drawings without this resulting in a restriction.

BRIEF DESCRIPTION OF THE DRAWINGS

Accompanying the specification are figures which assist in illustrating the embodiments of the invention, in which:

FIG. 1 contains a table of measurement results for a pocket probe that was arranged perpendicular to a glass surface at an output power of 15.5 mW;

FIG. 19 depicts the embodiment of FIG. 18 and illustrates two exemplary embodiments of applicators, whereby the applicator A illustrated at the top is a pocket probe similar to that in FIG. 2, while applicator B, illustrated therebelow, is a surface probe similar to that in FIG. 3;

FIG. 20 depicts the embodiment of FIG. 18 and illustrates a locking mechanism containing a rotationally symmetrical locking body 58 that has an "H"-shaped cross-section and that in its center has a hole 60 with a diameter that is 1.01+0.02 mm;

DETAILED DESCRIPTION OF THE INVENTION

FIG. 1 contains a table of measurement results for a pocket probe that was arranged perpendicular to a glass surface at an output power of 15.5 mW. The measured powers are provided in mW depending on the diameter of an optical fiber and the distance from the light source. It should be stated at this point that a photosensitizer with a high concentration is preferably used, specifically preferably greater than 0.1%, in particular on the order of magnitude of 1%, in a solvent, whereby in accordance with FIG. 1 methylene blue in solution is provided for the photosensitizer.

Figure 2:
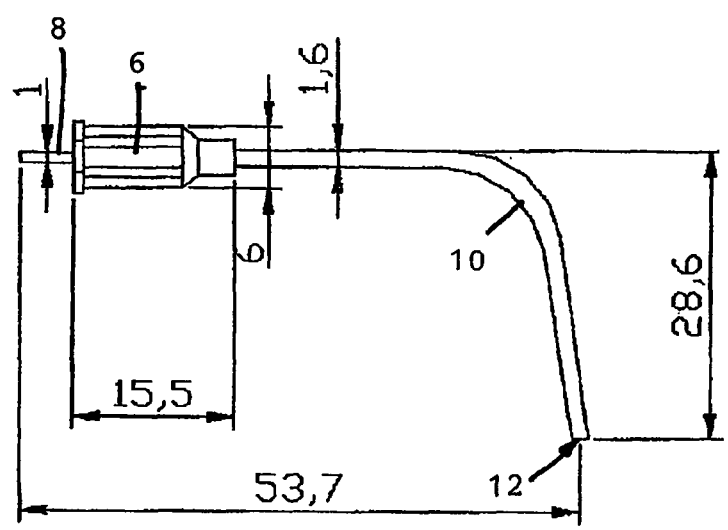
FIGS. 2 and 3 depict a pocket probe and a spot probe for applicators.
Figure 3:
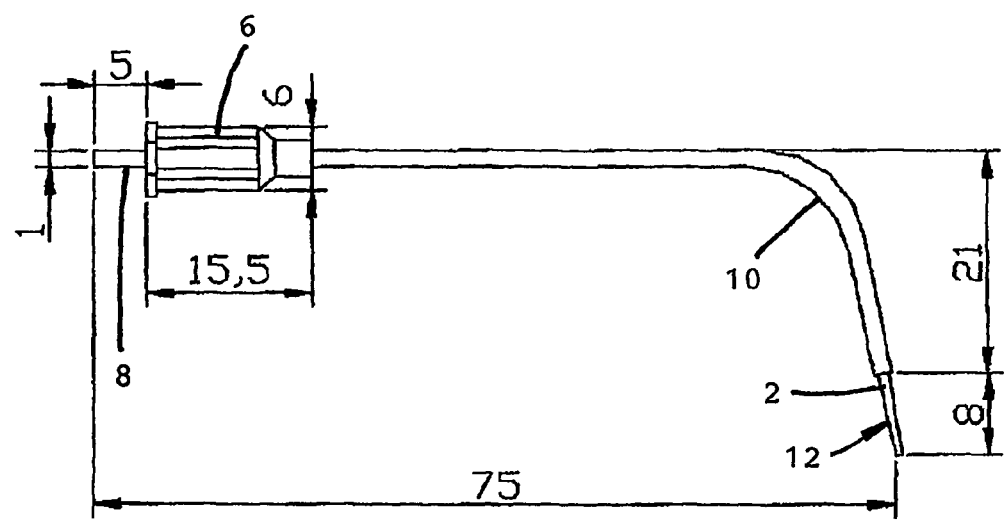

FIGS. 2 and 3 depict a pocket probe and a spot probe for applicators. It is understood that the dimensions provided in millimeters as examples here and in the other figures can be modified where needed. The applicators contain a light conductor 2 embodied as a fiber that is for the most part exteriorly surrounded by a protective jacket 4. The applicators furthermore have a connector body 6 that is preferably embodied as a Luer plug and that connects or is received in the head of the radiation device. The light conductor 2 passes through the connector body 6 and its end 8 projects beyond by a predetermined length, specifically by 5 mm in accordance with FIG. 2. The light conductor end 8 is not provided with a protective jacket and when the applicator is connected is inserted into the head part of the radiation device and positioned therein. The light conductor 2 is embodied at least partially flexible and/or contains a curved area 10. The dimensions of the applicators are provided such that they can be inserted into the oral cavity with no problem.

In the laser used in both applicators, the laser radiation exits in a circle with a 1-mm core diameter due to the material properties and the grinding geometry in the area of the tip 12 at an initial divergence angle ranging from 30 to 60°, preferably 40 to 55 degrees, frontally or in particular for the pocket probe ranging from 220 to 300 degrees, preferably 240 to 290°, in particular 260 to 280 degrees.

These properties render the applicators easy-to-use optical tools for precise irradiation of surfaces that have simple shapes, but also surfaces that have complex shapes.

Figure 4:
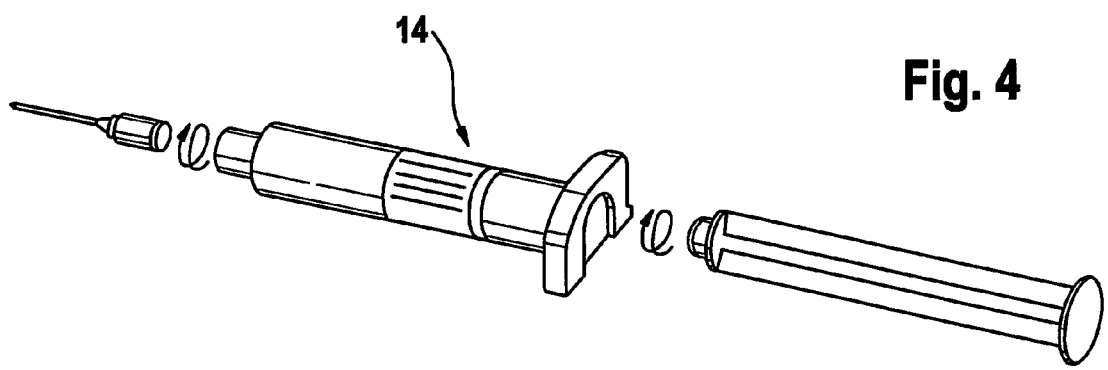
FIGS. 4 and 5 depict the structure and assembly of the application syringe 14 that contains the light-activatable substance in solution.
Figure 5:
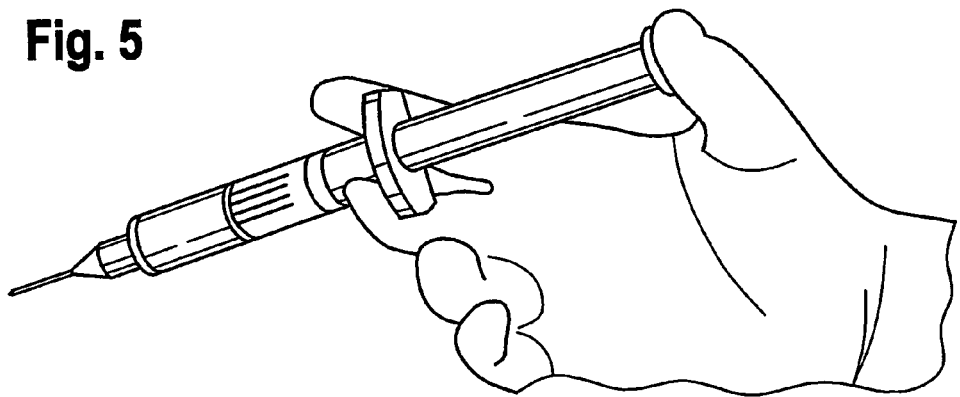

The structure and assembly of the application syringe 14 that contains the light-activatable substance in solution are depicted in FIGS. 4 and 5. The syringe 14 that contains the light-activatable substance in solution is supplied ready-to-use. Prior to use, the cap must be carefully rotated to remove it from the tip and the enclosed sterile cannula must be fixed on the Luer lock adapter of the syringe. Care should be taken that the fingers are correctly positioned. Carefully explain the procedure to the patient prior to treatment. Once the area to undergo therapy has been prepared properly in terms of clinical-surgical aspects, open the package; one blister-packet with the light-activatable substance, one blister-packet with a cannula, and any printed material are removed. Read the printed material prior to first use. Maintaining sterile conditions, empty both blister-packages over the sterile surgical tray. Syringe and cannula are thus sterile and ready for use in the sterile area. Carefully remove the silicon stopper from the syringe and fix the cannula by rotating on the Luer cone.

Figure 6:
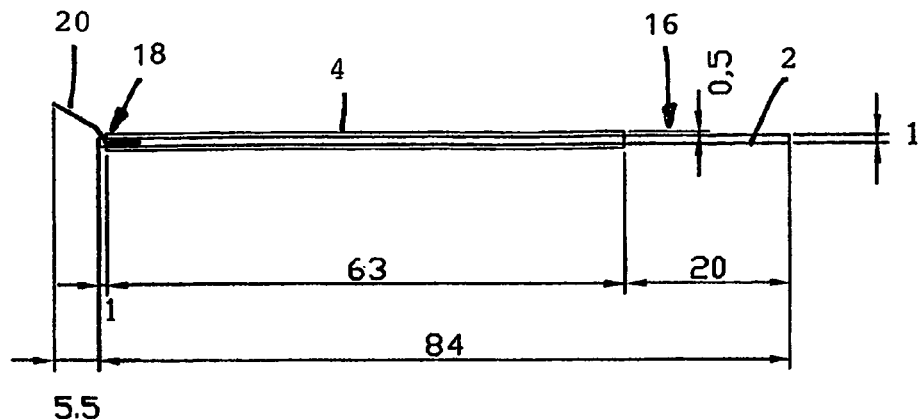
FIG. 6 depicts the light conductor piece of the applicator, not yet bent and without the connector body, which is arranged in the area 16.

FIG. 6 depicts the light conductor piece of the applicator, not yet bent and without the connector body, which is arranged in the area 16. The protective jacket 4 is provided between this area 16 and the free end 18. Furthermore, arranged at the free end 18 is a spacer 20 by means of which a defined distance is maintained from the area to undergo therapy, in this case 5.5 mm.

Figure 7:
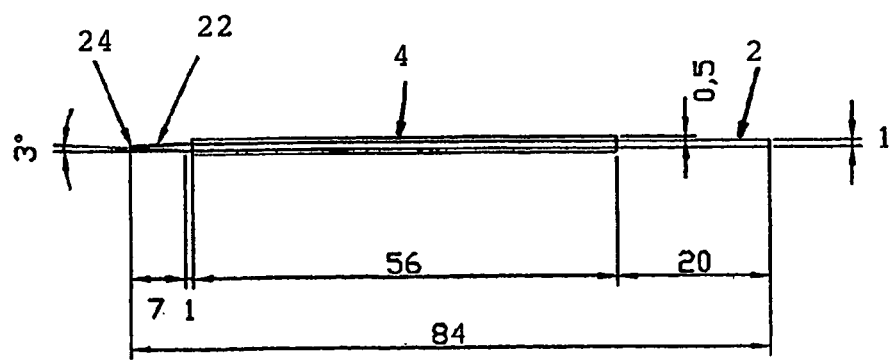
FIG. 7 depicts the light conductor piece for the pocket probe, the free end 22 being free of the protective jacket 4 and having a length of 7 mm.

FIG. 7 depicts the light conductor piece for the pocket probe, the free end 22 being free of the protective jacket 4 and having a length of 7 mm. The free end 22 is ground and has a surface with a 100 grain size, corresponding to processing with abrasive paper. The tip 24 of the free end 22 is embodied stub-like and/or is provided with a radius. The surface preferably has a predetermined micro-roughness. It preferably has an Ra value ranging between 10 and 40 μm, preferably ranging between 20 and 30 μm.

Figure 8:
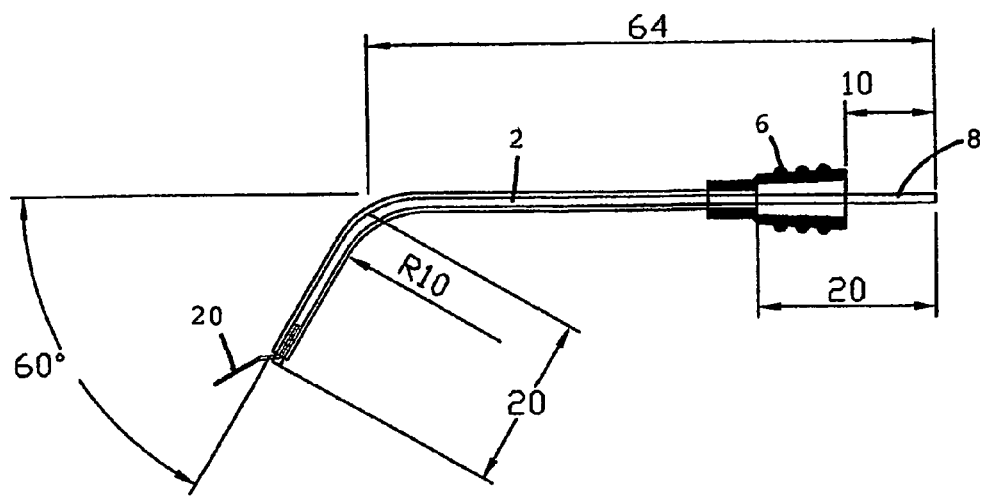
FIG. 8 depicts an applicator similar to FIG. 4, a spacer 20 being arranged on the free end.

FIG. 8 depicts an applicator similar to FIG. 4, a spacer 20 being arranged on the free end. In this embodiment, the light conductor end 8 projects from the connector body 6, specifically at a length of 10 mm.

Figure 9:
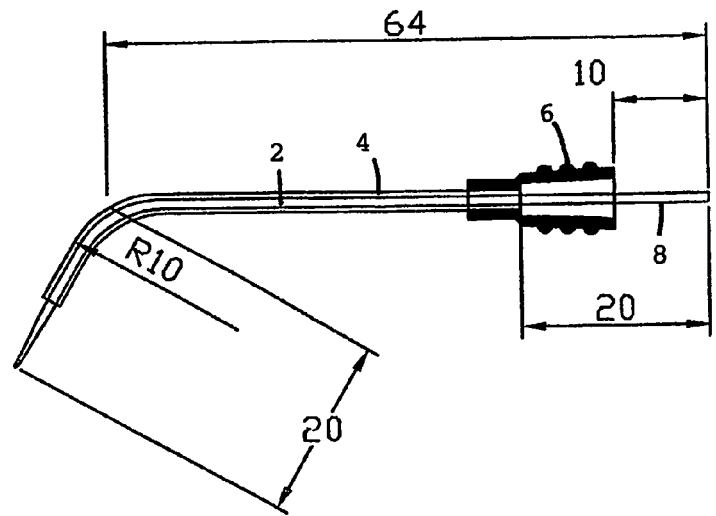
FIG. 9 depicts a bent light conductor piece of a pocket probe similar to that in FIG. 3, the free light conductor end 8 projecting from the connector body 6 at a predetermined length, in this case 10 mm.

FIG. 9 depicts a bent light conductor piece of a pocket probe similar to that in FIG. 3, the free light conductor end 8 projecting from the connector body 6 at a predetermined length, in this case 10 mm.

Figure 10:
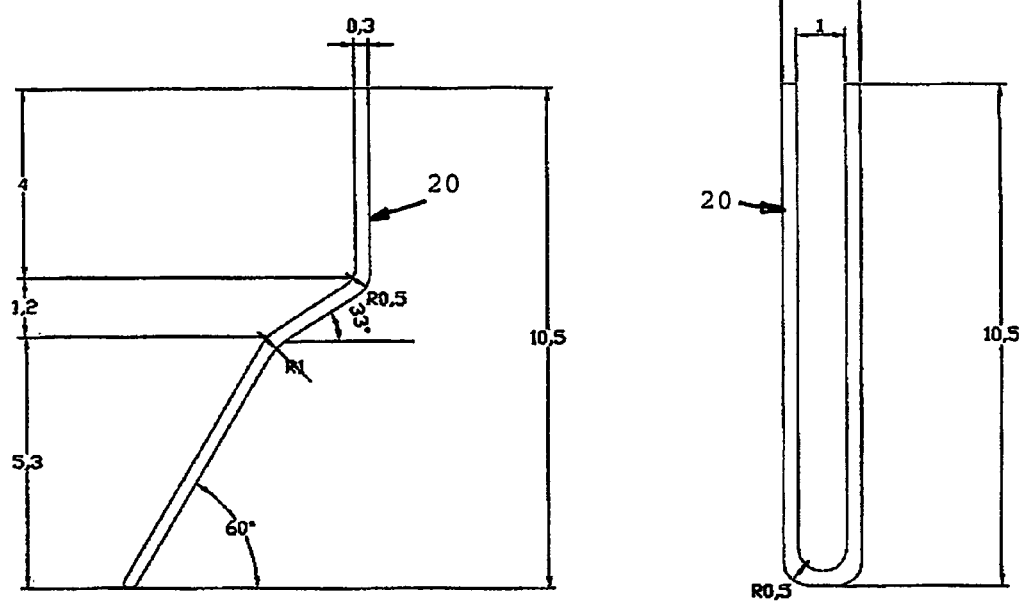
FIG. 10 depicts side elevations of one preferred embodiment of the spacer 20.

FIG. 10 depicts side elevations of one preferred embodiment of the spacer 20.

Figure 11:
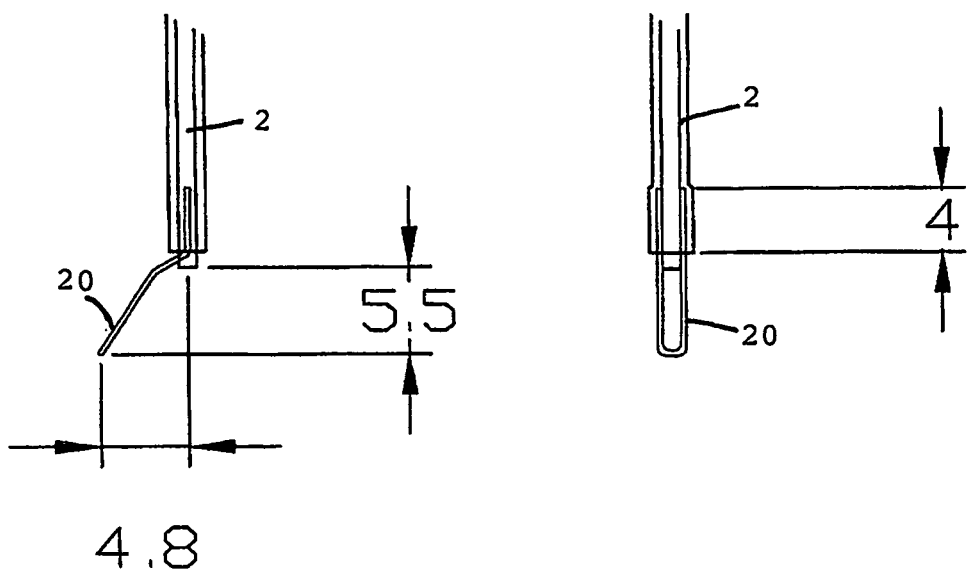
FIG. 11 depicts elevations of the surface probe with inwardly contracted light conductor with the spacer 20.

FIG. 11 depicts elevations of the surface probe with inwardly contracted light conductor with the spacer 20.

Figure 12:
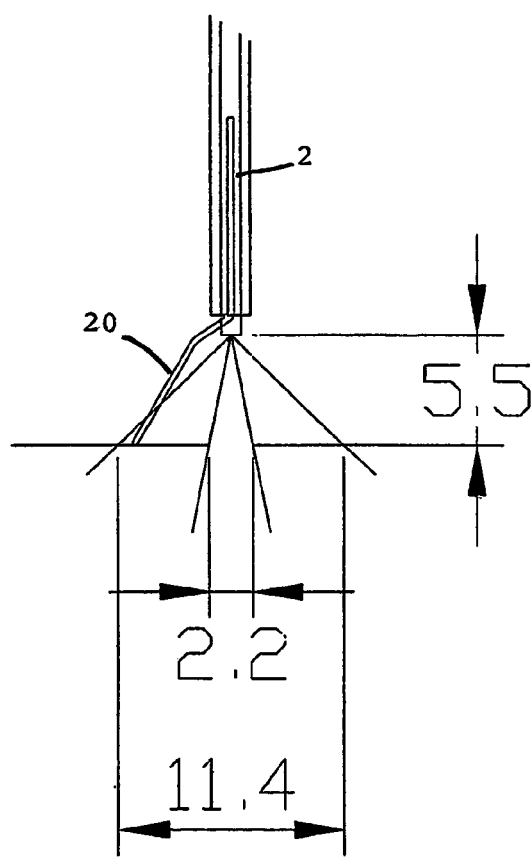
FIGS. 12 and 13 provide partial depictions of surface probes, whereby in accordance with FIG. 12 the surface probe has a numerical aperture of 0.72.
Figure 13:
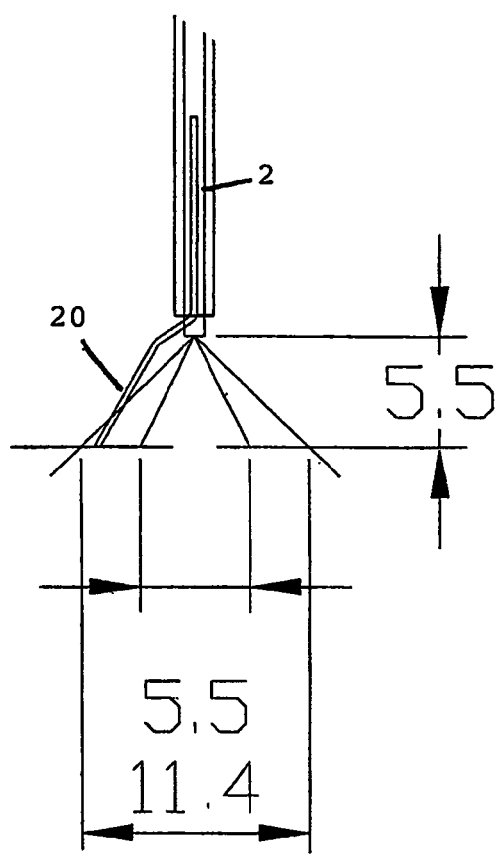

FIGS. 12 and 13 provide partial depictions of surface probes, whereby in accordance with FIG. 12 the surface probe has a numerical aperture of 0.72.

Figure 14:
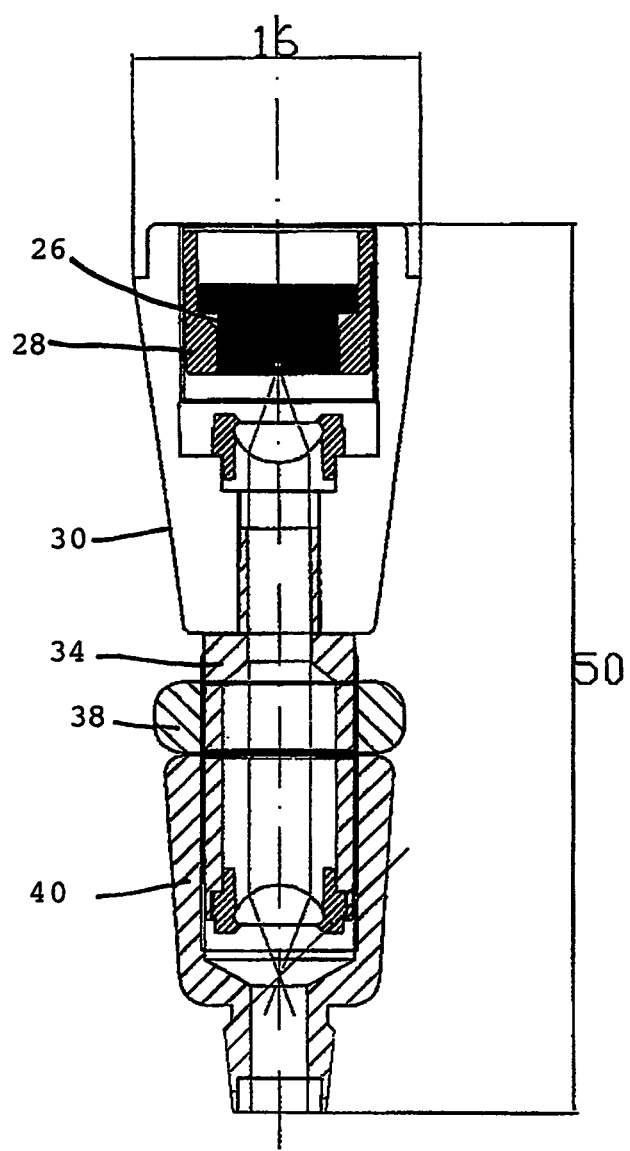
FIGS. 14, 15 and 16 depict the optical system of the radiation device, whereby in accordance with FIG. 14 a perpendicular beam divergence angle of no more than 35° is provided and in accordance with FIG. 15 a parallel beam divergence angle of no more than 10° is provided.
Figure 15:
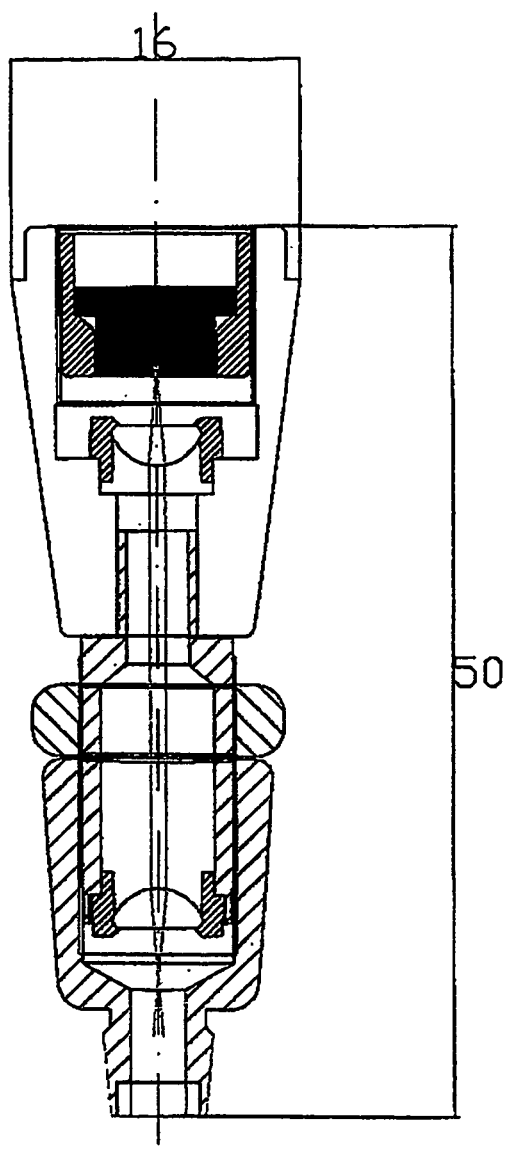
Figure 16:
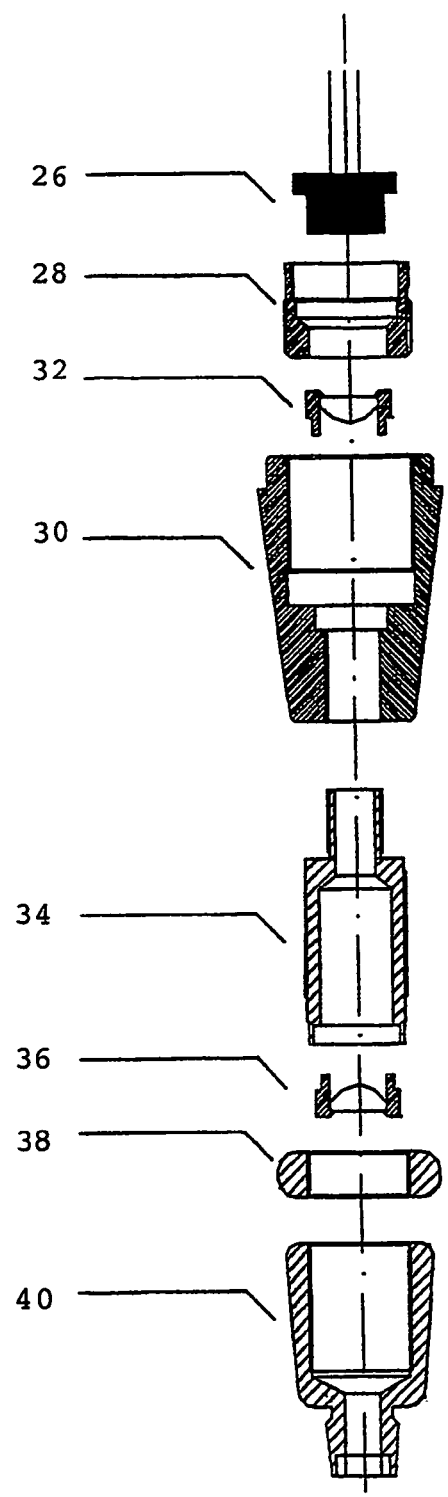

FIGS. 14 through 16 depict the optical system of the radiation device, whereby in accordance with FIG. 14 a perpendicular beam divergence angle of no more than 35° is provided and in accordance with FIG. 15 a parallel beam divergence angle of no more than 10° is provided. As can be seen in particular from the exploded illustration in accordance with FIG. 16, the laser diode 26 is arranged in a threaded sleeve 28. This is a multimode laser diode with 100 mW continuous for 670 nm including a monitor diode. There is an objective lens 32 in the tapered part 30, a lens holder 34 being provided for an additional objective lens 36. Furthermore provided are an adjusting ring 38 and a receiving body 40.

Figure 17:
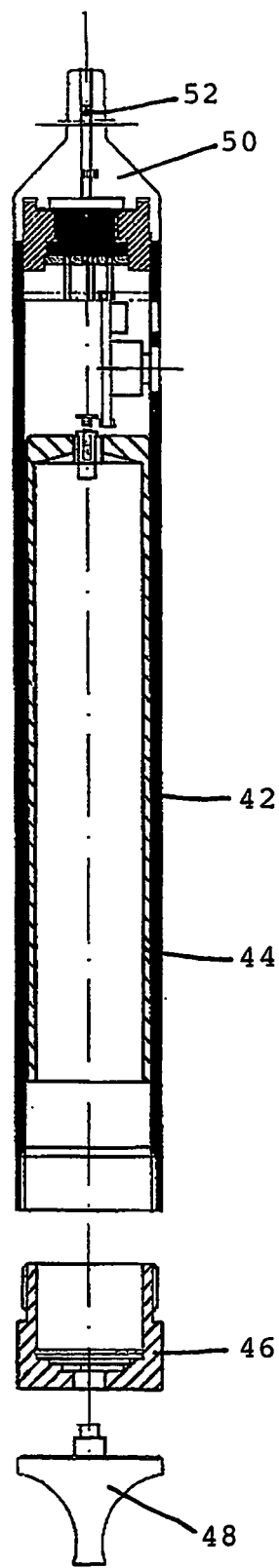
FIG. 17 illustrates the radiation device without the optical system, whereby a battery tube 44 for the batteries required for supplying current to the electronics is present in a housing tube 42.

FIG. 17 illustrates the radiation device without the optical system, whereby a battery tube 44 for the batteries required for supplying current to the electronics is present in a housing tube 42. A cap 46 is detachably connected or can be detachably connected to the housing tube 42 via a threaded connector at the posterior end, the lower end in accordance with the drawing, of the housing tube 42. Furthermore, a key-operated switch 48 is provided at the posterior end of the housing tube 42 or the cap 46 by means of which the irradiation or laser device can be turned on and off. Arranged at the anterior end of the housing tube, which is embodied as a protective housing, is a head part 50 that is embodied for receiving the applicators and for decoupling the light beam using the central bore 52.

The following light output is available for irradiation using the preferred embodiment of the radiation device, which is also called the HELBOTherLite laser:

|             | Pocket probe                                                                      | Spot probe                                                      |
| ----------- | --------------------------------------------------------------------------------- | --------------------------------------------------------------- |
| Irradiation | Radial, 250-280 degree range, in particular largely 270 degrees frontally         | 40-60 degree range, in particular largely 50 degrees frontally  |
| Power density | >40 mW/cm$^2$                                                                   | >40 mW/cm$^2$                                                   |

The preferably used light-activatable substance is a sterile, isotonic, deep blue odorless aqueous liquid. It contains phenothiazin-5-ium, 3,7-bis(dimethylamino)-chloride for coloring and sensitizing microorganisms for the lethal photodynamic therapy using the radiation device.

1 mL of the solution contains:

1% phenonthiazin-5-ium, 3,7-bis (dimethylamino)-, chloride

Glucose for isotonization

MHPC (methylhydroxypropylcellulose) for adjusting the viscosity

Citrate for buffering the solution

The osmolarity is approximately equal to that of human tissue.

The in solution with the light-activatable substance is packed in a glass syringe and sealed with a stopper made of silicon. The fill quantity is 0.5 mL+/−0.1 mL. The glass syringe is sealed with a blister and is steam-sterilized in a validated sterilization process. The aforesaid solution is usefully packaged in five blister-packs with one printed insert in a box. Five 28 G cannulas that are each also packed in a blister-pack and sterilized are also enclosed.

During the lethal photodynamic laser therapy, the light-activatable substance stains and sensitizes microorganisms in local superficial infections, in particular in the mouth, jaw, and facial areas. Subsequent irradiation with the radiation device eliminates stained microorganisms and restores the natural oral bacteria.

Topical application occurs in the area of the infection without or with a surgical incision and curettage and paralesional as follows: the patient rinses with water twice for 20 seconds. Saliva or blood adhering to the surfaces to be treated is suctioned or dabbed off in order to prevent dilution of the photoactive substance.

The light-activatable substance is slowly applied by means of the syringe, covering the surface of the infected tissue. The quantity must be selected such that the light-activatable substance moistens the surface of the infected areas in a layer that is as thin as possible. Make sure that the folds and pockets in the tissue are completely moistened. Where required, when the morphology is complex, carefully distribute with the air syringe. The light-activatable substance needs at least 60 sec to take effect. After rinsing for at least 3 sec while suctioning excess solution (deposits of stain must be removed!), irradiate with the radiation device. The correct dosage of energy supply, the irradiation, is essential for the germ-reducing effect and thus for treatment results.

The operator controls the therapy using treatment time for a given surface area treated as the critical variable for determining the required energy density (J/cm$^2$). For each cm$^2$ or tooth there should be at least 1 minute of irradiation time with the radiation device.

The following formulas are used for calculating the irradiated surface A of a lesion with a radius r during the irradiation:

a: with pocket probe: surface of defect F=Width W*Height*2 and thus per quadrant:

|  | Teeth | | | | | | | |
| --- | --- | --- | --- | --- | --- | --- | --- | --- |
|  | 1 | 2 | 3 | 4 | 5 | 6 | 7 | 8 |
| Width, cm | 0.6 | 1.2 | 1.8 | 2.4 | 3 | 3.6 | 4.2 | 4.8 |
| Height, cm | 0.8 | 0.8 | 0.8 | 0.8 | 0.8 | 0.8 | 0.8 | 0.8 |
| 3D factor | 2 | 2 | 2 | 2 | 2 | 2 | 2 | 2 |
| Surface area, cm$^2$ | 0.96 | 1.92 | 2.88 | 3.84 | 4.8 | 5.76 | 6.72 | 7.68 |
| Power, mW | 50 | 50 | 50 | 50 | 50 | 50 | 50 | 50 |
| Surface density, W/cm$^2$ | 0.052 | 0.052 | 0.052 | 0.052 | 0.052 | 0.052 | 0.052 | 0.052 |
| Irradiation, sec | 60 | 120 | 180 | 240 | 300 | 360 | 420 | 480 |
| Energy density, J/cm$^2$ | 3.125 | 3.125 | 3.13 | 3.125 | 3.125 | 3.125 | 3.125 | 3.125 |

Irradiation protocol for the pocket probe

B: with the spot probe: Surface of defect F=($\pi r2$)

The power density (FD) is calculated as follows:

FD (Watt/cm$^2$)=power (Watt)/irradiated surface (cm$^2$)

The energy density (ED) is calculated as follows:

ED (Wattsec/cm$^2$)=power (Watt)*time sec/irradiated surface (cm$^2$)

The dosimetry selected is consolidated in the following table. As a rule, irradiation is performed at a distance of 0.55 cm and at a power density of 0.051 W/cm$^2$ a total dose of 3 J/cm$^2$ is used.

| Irradiation unit | 1 | 1 | 1 | 2 | 3 | 4 | 5 | 6 |
| --- | --- | --- | --- | --- | --- | --- | --- | --- |
| Diameter, cm | 1.8 | 0.9 | 1 | 1 | 1 | 1 | 1 | 1 |
| Radius, cm | 0.9 | 0.45 | 0.5 | 0.5 | 0.5 | 0.5 | 0.5 | 0.5 |
| Distance, cm | 1 | 0.5 | 0.55 | 0.55 | 0.55 | 0.55 | 0.55 | 0.55 |
| Surface area, cm$^2$ | 2.5434 | 0.6359 | 0.79 | 1.57 | 2.355 | 3.14 | 3.925 | 4.71 |
| Power, mW | 40 | 40 | 40 | 40 | 40 | 40 | 40 | 40 |
| Surface density, W/cm$^2$ | 0.016 | 0.063 | 0.051 | 0.051 | 0.051 | 0.051 | 0.051 | 0.051 |
| Irradiation, sec | 60 | 60 | 60 | 120 | 180 | 240 | 300 | 360 |
| Energy density, J/cm$^2$ | 0.94 | 3.77 | 3.06 | 3.06 | 3.06 | 3.06 | 3.06 | 3.06 |

Irradiation Protocol for Spot Probe

An effective phototoxical effect can be induced if bacteria are stained using light-activatable substances or vital stains such as MB and irradiated with light of a suitable wavelength. Unstained cells do not demonstrate any toxic damage. Photochemical killing of possible pathogenic bacteria is performed at fur farms and zoos in that methylene blue is added to the drinking water.

MB has been used for 25 years as a photosensitizer for local treatment of herpes-induced illnesses. The dark toxicity and phototoxicity (PDT) of intratumorally applied methylene blue was explored in experiments on colon tumors. These tumors were not destroyed by irradiation alone with a low total dose (6 J/cm$^2$) or by administering the substance (20 μg/mL) alone.

Adding MB can lead to systemic secondary effects such as increased perspiration, nausea, and vomiting.

Oral administration can lead to gastrointestinal complaints and to dysuria. The ingredients for preparing the solution are:

| Active/inactive ingredients | 1 mL contains |
| --- | --- |
| Methylene blue × H2O | 10.00 |
| Trisodium citrate × 2 H2O | 0.433 |
| Citric acid × 1 H2O | 1.667 |
| MHPC | 10.00 |
| Sodium chloride | 9.00 |
| Water for injection | 1000 |

Ingredients of light-activatable substance:

Using the present biocompatibility assessment, the substances used in the preparation are evaluated with respect to their biocompatibility, teratogenity, and mutagenity under the given application conditions as acceptable in terms of the desired treatment goal.

Using topical application of the photosensitizer (PS), there are none of the significant problems associated with systemic use of a medication such as antibiotics, nor of systemically used PS, such as e.g. substance toxicity and generalized multi-week photosensitization of the skin. Topical application increases specificity so that healthy tissue, e.g. mucosa in the area surrounding the lesion, is protected.

The treatment can be repeated due to the minor nature of the secondary effects. The therapy is furthermore distinguished by its non-invasive nature.

The local concentration is also influenced in that as a rule increased salivation is induced in the oral mucosa after local application of the PS. This leads to a decrease in the PC concentration and reduces the stain's penetration into the lesion. Moreover, saliva proteins can deactivate the PS because of non-specific binding. Introducing the PS in a solution, in particular a viscous solution, inventively reduces the mixing, dilution, and reaction with saliva for the treatment period.

After the period for taking effect, which is at least 60 sec, in accordance with the invention the excess PS is removed in order to increase the light transparency of the treated tissue.

Measurements demonstrate that a 100-μm liquid film of the solution with the light-activating substance that stands on the tissue reduces the effective energy density by 97%. In accordance with the Beer-Lambert Law, the light is further weakened when the layer thickness is doubled. Thus therapeutically effective irradiation is not possible with the light-activating substance when there is excess solution.

An energy density of 50-100 J/cm$^2$ is recommended for effectively applying PDT to oral mucosa lesions. The energy dose should be matched to the type and localization of findings. Since the oral mucosa are generally very sensitive to pain, power densities greater than 150 mW/cm$^2$ should be avoided. Power densities between 200 and 500 mW/cm$^2$ can lead to non-specific thermal tissue damage.

The surface area irradiated should be selected to be larger than the surface area of the lesion in order to attain a uniform dose in the area of the lesion.

The light dose of approximately 100 J/cm$^2$ for the PDT can be attained in different manners: high power density and short exposure times or low power density and long exposure times. Due to the aforesaid thermal damage, high powers are not used. On the other hand, it is not possible to obtain a photodynamic effect when the power densities are too low, even if the irradiation periods are correspondingly long.

Methylene blue solutions are able to reduce the number of all examined microorganisms in the culture medium being used.

Methylene blue solutions reduce almost all Gram positive bacteria in a concentration of 25-44 μmol in vitro.

Completely reducing Gram negative germs requires 3-30 times higher concentrations. *P. aeruginosa* was reduced from 100 mW/cm$^2$ by 3.5 $\log_{10}$ CFU at a concentration of 200-mol and an energy density of 100 mW/cm$^2$.

The observed dark toxicity was higher for toluidine blue (TB) than for methylene blue (MB). This is consistent with the distribution coefficient P that was determined to be 0.33 for TB and 0.11 for MB.

Since log P was <0, both stains can be characterized as hydrophilic and, at least theoretically, should be able to fit the water-filled porin protein channels of Gram negative bacteria.

While dark toxicity for Gram positive bacteria was nearly unrelated to type, the dark toxicity for Gram negative bacteria is quite clearly a function of type and specifically corresponds to the trans-membrane permeability coefficient of the exterior membrane of Gram negative bacteria.

Dark toxicity was a function of both the concentration and the incubation period prior to irradiation.

*S. aureus* was identified as the most resistant bacterium for the Gram positive group, and it required the highest concentrations for its destruction.

*P. aeruginosa* was identified as the most resistant bacterium for the Gram negative group, and it required the highest concentrations for its destruction.

In the case of Gram negative bacteria, photodynamic sensitivity is a function of trans-membrane permeability, and hydrophilicity, positive charge, and low molecular weight of the stain molecule promote efficacy.

For the present therapy, only 60-sec periods for taking effect with subsequent rinsing prior to irradiation are provided for the treatment of microbially infected areas.

The selected parameters of therapy, in particular:

1% concentration of the light-activating substance in solution

Energy of 2.4 J

Power density of 50 mW/cm$^2$

And energy density of 3 J/cm$^2$

Incubation time of 60 sec with subsequent rinsing of solution are suitable for assuring a positive treatment result. On the other hand, possible risks and secondary effects are limited when these conditions are observed and, when properly explained, seem to be acceptable in light of the expected positive aspects for patients.

PDT is based on a photochemical process in which the photosensitizers (PS) are activated by means of laser radiation and the radiated energy "portions" such that it is available for forming locally toxically acting oxygen radicals. Thermal damage to the tissue can be prevented with certainty at the selected energy and power densities of 3 J/cm² and 50 mW/cm², respectively.

The clinical application of PDT is possible since the stain solutions selectively color cell systems, while the interaction with the epithelium is very limited. Studies of normal oral mucosa indicated that the penetration depth of MB solutions after 10-min incubation time was limited to just the first 1-2 exterior layers of cells of the epithelium. Furthermore, the life expectancy of the active radicals and their precursors is microseconds, so that it is practically assured that there are no concomitant destructive effects in healthy tissue due to diffusion, since there is not enough time for this.

The effect is thus linked to the presence of the stain molecule in the PS.

The selection of for instance methylene blue for the photodynamic active substance in the preparation is based, first, on the low toxicity of methylene blue under the selected conditions, and second, on the favorable absorption maximum at 664 nm:

Capable and efficient diodes for producing the laser beam are available for this wavelength Treatment is performed in the visible light spectrum, which is crucial for the therapy's safety and efficiency The depth the light penetrates into the tissue in this wavelength range is adequate for also being able to reach penetrating bacterial colonies The singulet oxygen formation is the critical mechanism for killing the germs, while healthy cells cause these radicals to deteriorate due to catalases Can, on the other hand also be some protection due to the efficacy of vitamins like vitamin C and E.

Given the results of the spectro-photometric tests of MB with and without irradiation, there was a nearly linear decrease in extinction as applied energy density increased. Photo-bleaching with destruction of the stain molecules occurs to a significant extent at energy densities that are greater than the therapeutically applied energy density by a factor of 7.

A photo-biological effect occurs in this area that promotes tissue regeneration and stabilizes local metabolism Methylene blue is available in a pure and documented form the use in a preparation leads to stable solutions These solutions are simple and safe to handle under conditions prevalent in medical surroundings when used with appropriate caution The waste that occurs during use is relatively harmless Coordinating stain and light source provides a therapeutically effective system that demonstrates effectiveness against Gram positive and Gram negative bacteria as well as against fungus such as candida albicans and that, by reducing the number of microorganisms, supports the body's own defense for a short period in order to improve clinical symptoms.

Using the HELBO PocketProbe applicators, it is possible to inventively apply an energy density largely ranging from 1 to 7 J/cm², preferably from 2 to 4 J/m2, in particular a largely uniform energy density of 3 J/cm², even in complex sites around and between teeth in the posterior areas of the oral cavity.

By using the photo-dynamic therapy, it was possible to observe rapid freedom from pain and accelerated wound healing due to supporting photo-biological effects.

The only secondary effects observed during the therapy were occasional burns; these healed rapidly after the treatment concluded, however.

One particular embodiment of the invention is described in greater detail in the following using FIGS. 18 through 27. The radiation device, which is also called the therapy laser hereinafter, is for photo-dynamic therapy (PDT) and is in particular embodied as a laser device. It contains a blocking device by means of which the light path is automatically uncovered when an applicator that contains a light conductor is attached. As long as the applicator and/or the light conductor is not attached to the radiation device/laser device, the inventively embodied blocking device prevents laser light from exiting from the laser device. The blocking device in particular contains a locking body that is embodied and arranged such that laser light cannot exit unless the applicator or light conductor is attached. The locking body of the blocking device is arranged in a changeable position, and it cannot be moved from this position for uncovering the light path unless the applicator or light conductor is properly attached. The blocking device is in particular integrated in the head part of the radiation device. Alternatively, the blocking device can be at another location on the radiation device and/or embodied differently, and in particular can be integrated into the optical system. The inventive radiation device assures that the light is coupled directly from the diode or laser diode into the light conductor such that 1. low losses occur because an optical fiber with a high numerical aperture is used, in particular greater than 0.5, preferably greater than 0.7, which ensures that a relatively large surface area is uniformly irradiated because the light beam opens up when it exits the fiber, 2. because of the installed blocking device, the light cannot exit unless the light conductor is inserted or attached, and otherwise the light cannot exit directly out of the laser device. Thus the laser device can be operated without protective goggles and without having to designate a Laser Protection Representative, as would fundamentally be necessary at the provided laser device output.

Due to the high numerical aperture of the light conductor used, the aforesaid scatter effect is attained when the light exits/when the area to undergo therapy is irradiated and on the side of the applicator or light conductor facing the laser device there is a collective effect such that a lens system between the laser or diode and the light conductor is not necessary.

When using the radiation or laser device and/or when using the arrangement for photo-dynamic therapy, the following listed steps are particularly important:

1. First apply the solution with the photosensitizer in a high concentration to the area to undergo therapy so that the solution penetrates as rapidly as possible, especially into the plaque on teeth.

2. In addition, it is preferred that there be rinsing with a medium, in particular water, with an ion concentration that is as low as possible so that bacteria and/or cell membranes are weakened due to the osmotic pressure gradients thus produced. It should be stated that for instance a physiological table salt solution would not work well due to the relatively high ion concentration. The pH of the medium is preferably alkaline. The pH is preferably 7 to 9. The oxygen partial pressure is preferably high. In the framework of the invention, the medium, in particular prepared tap water, has an oxygen partial pressure ranging from 4 to 6 mg/L for rinsing. The medium is usefully enriched with molecular oxygen up to 14 mg/mL. Furthermore, peroxide enrichment has proved useful in accordance with the invention, specifically as 0.5% to 3% hydrogen peroxide solution.

3. Due to the prior rinsing with a medium of low concentration, optimum cell damage occurs during the irradiation by means of the laser light.

Description of the irradiation device or laser device

Figure 18:
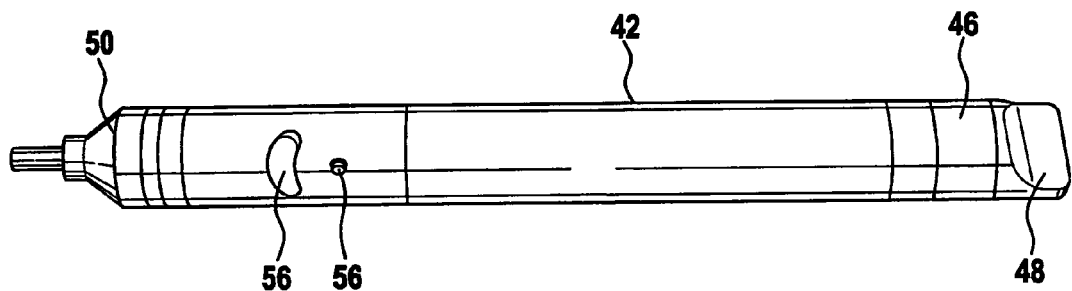
FIG. 18 depicts one particular embodiment of the invention and illustrates the radiation or laser device from the side, without applicator.
Figure 21:
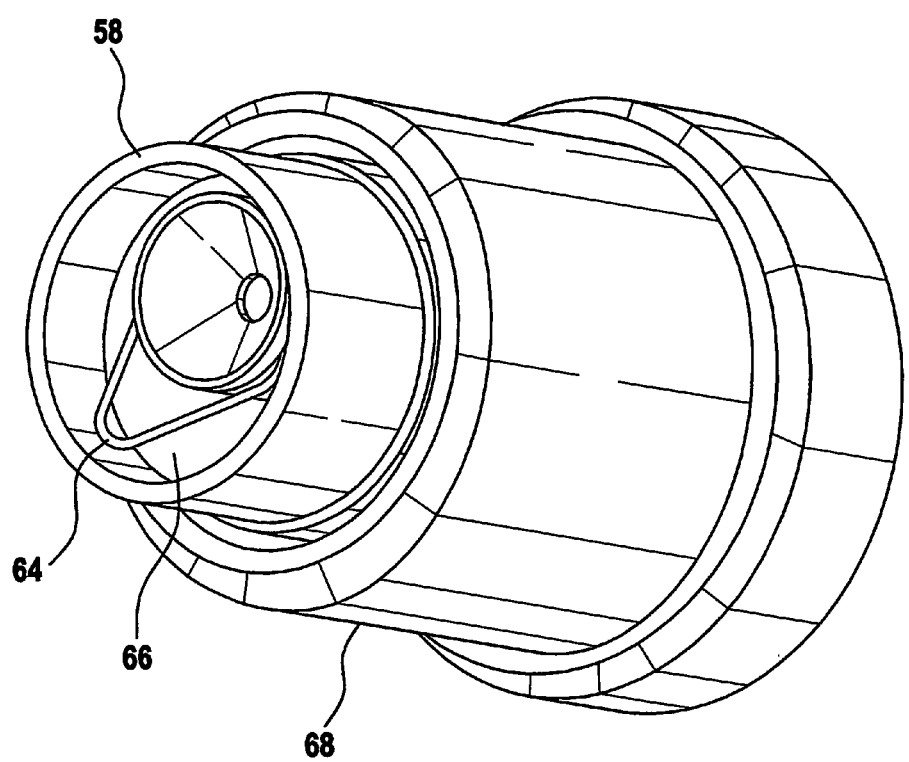
FIG. 21 depicts the embodiment of FIG. 18 and provides the exploded illustration of the locking body 58.
Figure 22:
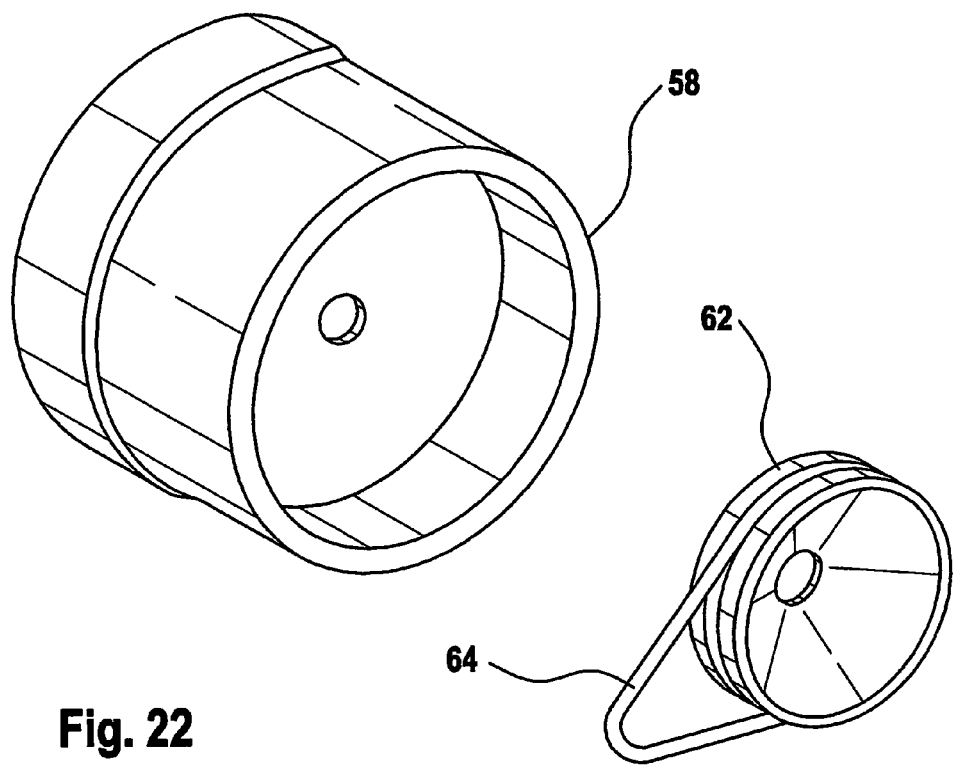
FIG. 22 depicts the embodiment of FIG. 18 and illustrates the locking disk 62 in FIG. 22.

The device is operated with batteries or accumulators and for the light or beam source uses a semiconductor laser (laser diode) that is operated continuously (cw). FIG. 18 illustrates the radiation or laser device from the side, without applicator. The beam source is built into a cylindrical protective metal housing 42. The length of the protective housing containing the housing tube 42 is about 124 mm, the diameter is about 16 mm. After the batteries or accumulators have been inserted, a contact cap 46 is screwed onto the end of the protective housing 42 where the batteries are to be inserted. Placing the key-operated switch 48 formed as the closure cap into the contact cap 46 renders the unit ready to operate. The operating mode is indicated by differently colored LEDs 54.

The head part 50 is screwed onto the protective housing 42 at the other end of the protective housing 42 and glued thereto so that direct access to the beam source is prevented. The head part 50 receives the applicators and is thus for coupling the laser beam, and it also contains the locking mechanism. Pressing a button 56 activates the semiconductor laser.

Applicators

FIG. 19 depicts two exemplary embodiments of applicators, whereby the applicator A illustrated at the top is a pocket probe similar to that in FIG. 2, while applicator B, illustrated therebelow, is a surface probe similar to that in FIG. 3. Both applicators comprise a transparent plastic light conductor with a diameter of about 1 mm, have a Luer plug for being received on the head of the laser device, are bent, and are surrounded with a white protective jacket between Luer plug and beam exit end. The light conductor end (without protective jacket) in the Luer plug is inserted into the head of the protective housing.

Applicator A has a slightly conical tip, the surface of which is roughened on the last 5 mm. The rough surface ensures that the laser light is emitted in nearly all spatial directions, the most energy being emitted in the axial direction of the light conductor. Applicator B has a flat end face as the exit surface for the laser light. In addition, a wire loop is built-in on the light conductor end as a spacer. In contrast to applicator A, the laser light has diverging, conical radiation characteristics, which means more energy is emitted in the axial direction. Therefore applicator B was used for all other measurements, since it contains the greater potential for risk from the standpoint of laser safety.

Blocking device/locking mechanism

The locking mechanism depicted in FIG. 20 contains a rotationally symmetrical locking body 58 that has an "H"-shaped cross-section and that in its center has a hole 60 with a diameter that is 1.01+0.02 mm. The laser diode is positioned in the recess of the "h" that faces away from the beam exit and in the activated condition emits light through the hole 60 in the locking body 58 in the direction of the beam exit.

Located in the depression of the "H" that faces the beam exit is a round locking disk 62 that also has in its center a hole with a diameter that is 1.01+0.02 mm. The exterior diameter of this disk 62 is substantially smaller than the interior diameter of the locking body 58, so that in accordance with FIG. 20 the disk can be placed in the depression. The locking disk is held eccentricially by means of a wire spring (locking spring), however. Thus this disk 62 covers the hole in the locking body and the laser light cannot exit. The wire spring 64 is conducted in a groove on the circumference of the locking disk. As can be seen from FIG. 21 and the exploded illustration of the locking body 58 and the locking disk 62 in FIG. 22, the locking body 58, in whose recess the locking disk is movably arranged, is arranged in a diode holder 68. In the exploded depiction in FIG. 22, it is easy to see the two aforesaid holes of the locking body 58 and locking disk 62.

It is not until the light conductor of the applicator is inserted up to the stop that the locking disk 62 is pressed into the central position so that the hole of the locking disk 62 and the hole of the locking body 58 coincide and the laser light can be coupled into the light conductor. If the light conductor is withdrawn, then the wire spring 64 presses the locking disk 62 back into the starting position and the laser light is blocked. In the framework of the invention, other restoring elements can also be provided instead of the wire spring 64 depicted here in order to make it possible for the laser light to exit only when the applicator and in particular its light conductor end are properly connected to the radiation device.

Figure 23:
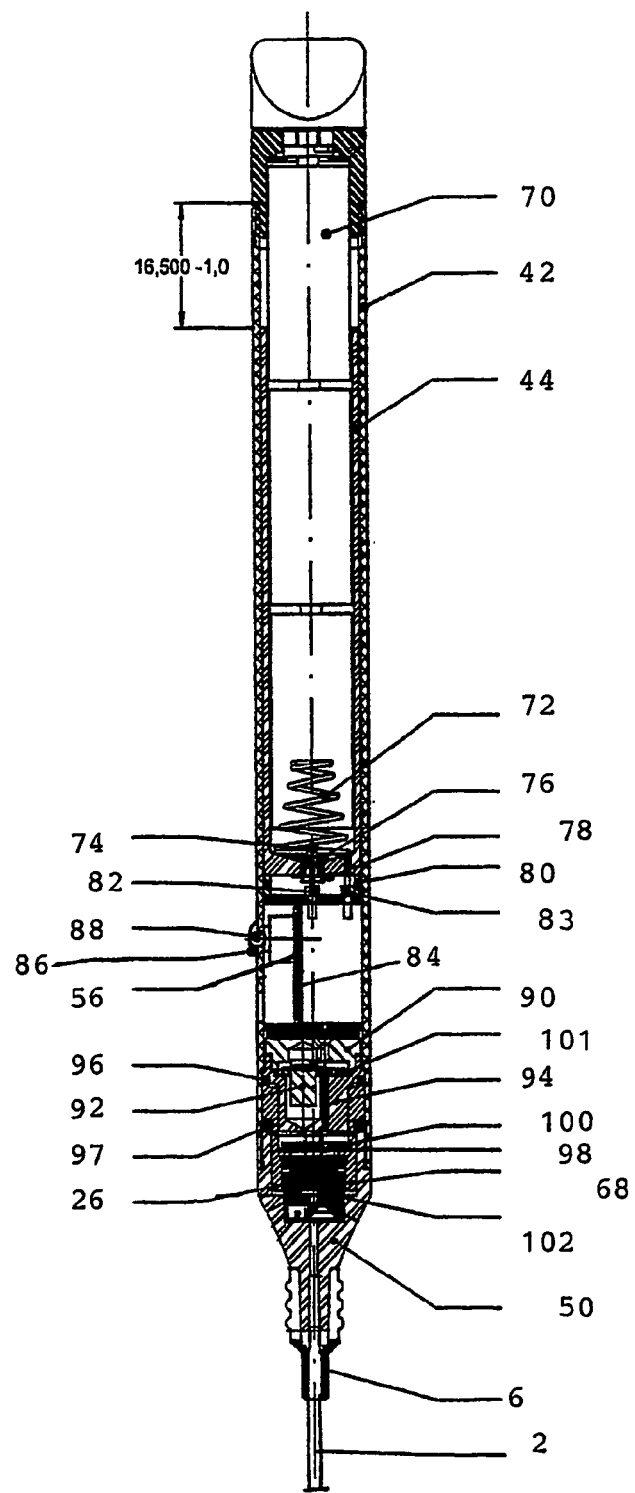
FIG. 23 depicts the embodiment of FIG. 18 and illustrates a section through the radiation device.
Figure 24:
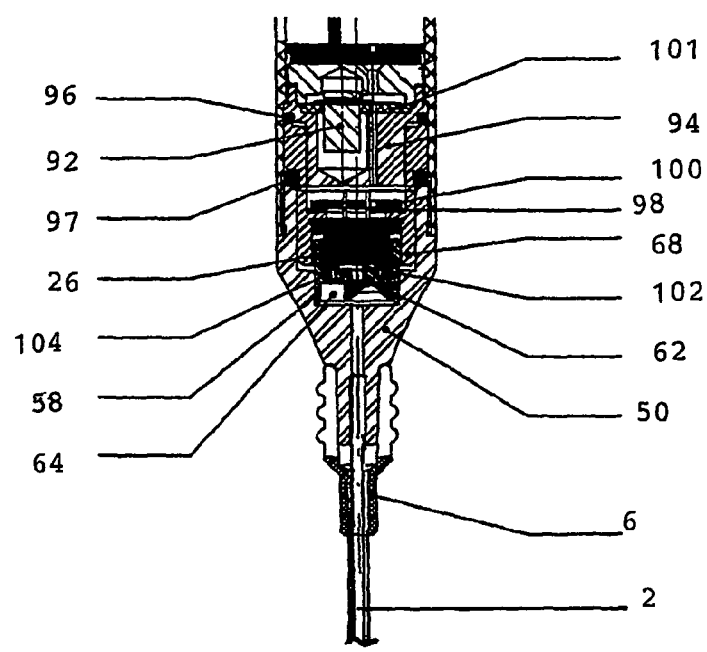
FIG. 24 is an enlargement of the anterior part of the device in FIG. 23.

FIG. 23 depicts a section through the radiation device and FIG. 24 is an enlargement of its anterior part. This radiation device fundamentally corresponds to that explained in the foregoing and additionally contains the blocking device/locking mechanism. Arranged in the battery tube 44 that is enclosed by the housing tube 42 are three batteries 70 that are actuated by means of a battery spring 72. A socket 74 is arranged in a guide 76, whereby furthermore present are a disk 78 and a spacing disk 80. Furthermore, two pins 82, 83 are provided for contacting with electronics or an electronic bar 84. The button 56 that can be actuated from outside is arranged on the electronics bar 84, whereby in particular for sealing of a key film 86 together with a ball 88 are provided. An area with a hammer 92 is provided in the anterior direction adjacent to the interior area with the electronics 84 and separated by means of a rear insulation 90, whereby an anterior insulation is also present. Two O-rings 96, 97 are furthermore arranged inside the housing tube 42. Arranged at the anterior end of the housing tube 42 is the head part 50, the anterior end of which engages in the connector body or Luer plug 4 of the applicator (not shown here). The diode holder 68, already explained in the foregoing, with the laser diode 26 is arranged in the head part 50, whereby an insulating disk 98 and a printed board 100 for the diode, including wires necessary for contacting, are provided to the rear toward the battery tube 44. In addition, provided in the direction of radiation in front of the laser diode is a protective film 102 by means of which in a preferred manner the laser diode can be protected against exterior influences, an O-ring 104 also being provided. Moreover, the locking disk 62 and the locking spring 64 are arranged in the interior recess of the head part 50 of the locking body 58, already explained.

Figure 25:
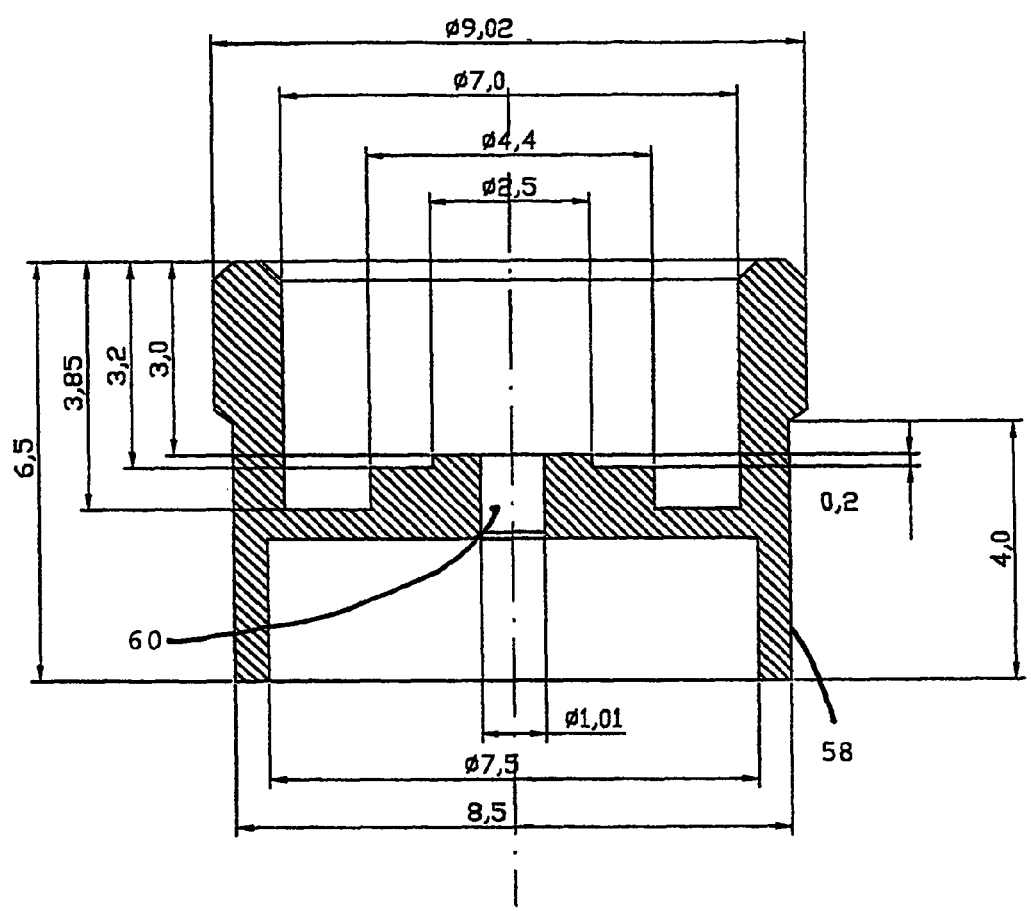
FIG. 25 depicts the embodiment of FIG. 18 and illustrates a section in an axial plane through the locking body 58, whereby it is easy to see the H-shaped sectional surface.

FIG. 25 depicts a section in an axial plane through the locking body 58, whereby it is easy to see the H-shaped sectional surface. It is understood that the dimensions given for the special embodiment in millimeters can also be different.

Figure 26:
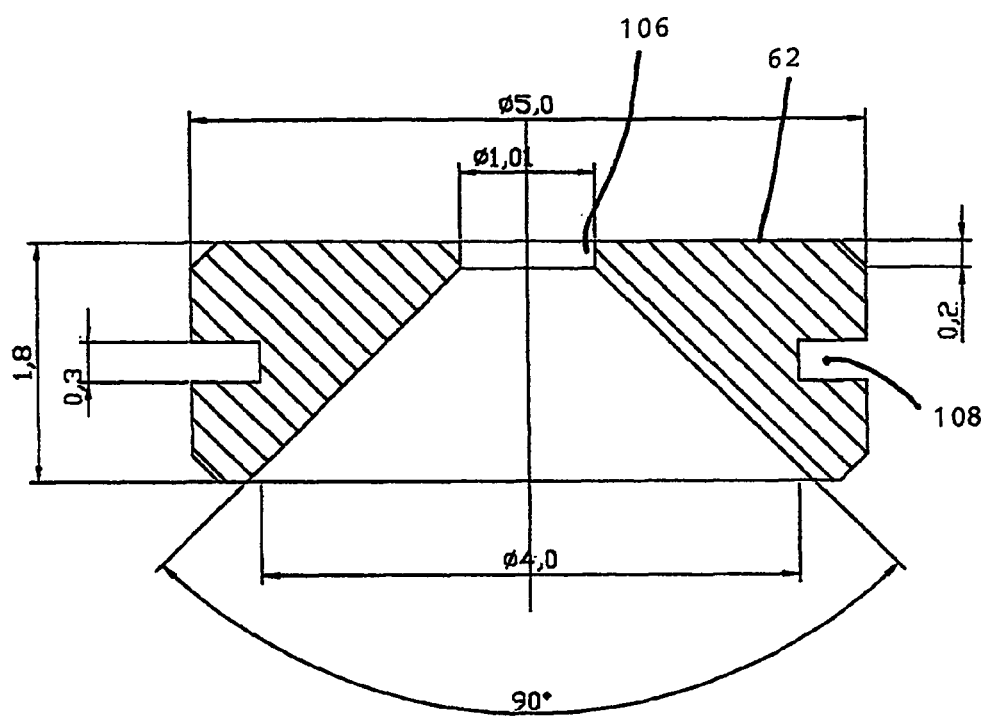
FIG. 26 depicts the embodiment of FIG. 18 and illustrates a section in an axial plane through the locking disk 62 that contains the hole 106, already described, in the center.

FIG. 26 depicts a section in an axial plane through the locking disk 62 that contains the hole 106, already described, in the center. On its exterior circumference the locking disk has a groove 108 in which the wire or locking spring engages.

Figure 27:
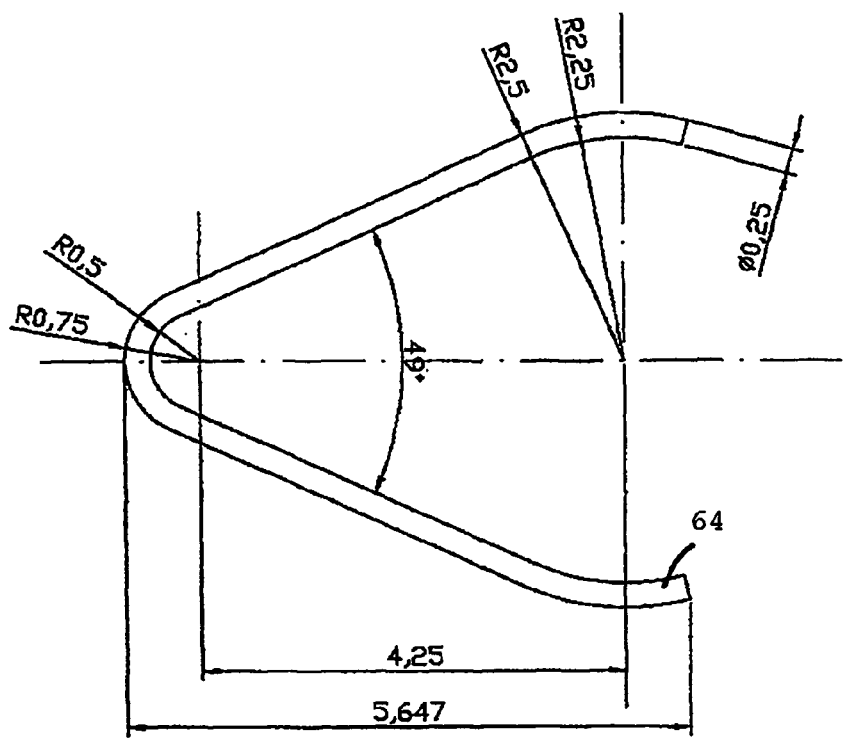
FIG. 27 depicts the embodiment of FIG. 18 and illustrates the locking spring 64.

Finally, FIG. 27 is a depiction of the locking spring 64. It does not have to be particularly stressed that the dimensions of the locking spring and the other components can also be different for other embodiments.

Functional description—blocking device

The blocking device contains the following individual parts:

Locking plate/locking disk
Spring blocking device/locking spring
Locking holder/locking body
Diode holder/diode holder
Diode
Head R60/head for Luer plug The parts are arranged as follows:

The diode is inserted in the diode holder and fixed from behind with the ESD bar. The diode is now seated in the diode holder. The diode is oriented over the interior diameter of the diode holder. Now the locking holder can be pushed onto the diode. The locking holder is positioned over the interior diameter of the diode holder. The O-ring in the locking holder absorbs minor shocks in the longitudinal direction.

The locking spring is inserted into the groove of the locking plate. This arrangement is placed into the opening of the locking holder. The head is pushed over the locking holder and the diode holder.

Functional description:

The light conductor is inserted into the light conductor path via the 1.5 mm bore in the head. After approx. 7 mm, the light conductor is positioned via a decrease in the diameter to 1.1 mm. The light conductor is then pushed to the locking plate.

The locking plate is pressed onto the interior edge of the locking holder by the pre-stress of the spring. The plate is always uncentered by this and covers the 1.01 mm bore in the locking holder so that no radiation can exit.

The light conductor strikes the cone of the locking plate and presses the latter against the spring force into the center of the locking holder. After the locking plate has been centered, the 1.01 mm bore of the locking holder is uncovered and the light conductor is pushed through this opening into the coupling area. The light conductor has reached the coupling area when the Luer plug reaches the stop on the head.

When the light conductor is withdrawn, the locking spring returns the plate to the non-central position, re-closing the 1.01 mm bore.

Discussion about the safety of the locking mechanism

The spring wire in the locking spring has a diameter of 0.25 mm. The groove is 0.3 mm. Since the wire has a round shape, it cannot become jammed in the groove. This means the blocking device is reliable. The edges of the locking plate are broken by slide grinding to 0.2 mm.

The spring always presses the locking plate outward. There is even locking without the locking spring due to the position of the laser during operation. The locking plate is pulled downward by its weight, closing the 1.01 mm bore. Because of the special shape of the spring, it is also not possible for the spring to jump out of the groove. The shape of the spring encloses the locking plate and then secures it.

Because of the slight angle, any incline in the plate has no effect on the locking mechanism. The plate moves back to its position the next time the light conductor is inserted.

Soiling on the locking mechanism has no effect on the function of the lock. The only factor that has to be taken into account is the dust from wear in the light conductor. A simple cleaning of the mechanism can be performed during the annual examination.

The only foreign bodies than can occur are 1.1 mm in size, since this is the limiting size for the bore in the head.

Any reduction in the spring force is monitored using tests. Changes caused by falls to the ground are also monitored.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. An arrangement for reducing microorganisms, comprising:
    an irradiation device, which comprises a light source and a first connector body;
    a rotationally symmetric locking body having a first recess within which is positioned the light source, having a second recess within which is positioned a locking disk, and having a wall separating the light source and the locking disk, the wall having an opening through which light from the light source passes; and
    at least one applicator;
    wherein the locking disk is eccentrically positioned within the second recess by a wire spring to block light from exiting the opening;
    wherein the wire spring is mounted within a groove of the locking member in the second recess;
    wherein the locking disk has a conical surface with an opening at an apex of the conical surface;
    wherein the applicator comprises a light guide surrounded by a protective jacket and a second connector body, by means of which the applicator is detachably connected to the irradiation device via the first connector body thereof;
    wherein the first connector body and the second connector body correspond to each other and interlock with one another in such a way that the light of the light source can be irradiated through the light guide to a therapy site, onto which a light-activatable substance has been applied for therapeutic purposes;
    wherein upon insertion of said applicator the light guide is guided by the conical surface into the opening at the apex biasing the locking disk into an alignment of the wall opening and the locking disk opening;
    wherein for therapy of a region of the oral cavity, the light guide has a numerical aperture greater than 0.5 and one end free of the protective jacket, wherein the light beam emanating from the light guide diverges, the dimensions of the applicator are specified so that it can be introduced into the oral cavity without difficulty and configured as a pocket probe having a pointed conical tip or as a flat probe;
    wherein the irradiation device comprises a housing tube and a head part situated at the front end thereof, which is configured as the first connector body;
    wherein the light source and an electronic circuit board having an externally actuatable button are located in the front part of the housing tube; and
    wherein batteries or rechargeable batteries for supplying the electronic units for the light source with power are further provided in the housing tube, with a cap being detachably connected to the rear end of the housing tube via a threaded joint.

2. The arrangement according to claim 1, wherein the light source is a laser diode, and wherein light from the laser diode is coupled into the applicator either directly or via a lens package.

3. The arrangement according to claim 1, wherein the head part for receiving the applicator and light outcoupling is formed by a central borehole and/or that a front end of the head part engages with the second connector body.

4. An arrangement according to claim 1, wherein the central borehole is designed to receive and/or center the light guide end of the applicator.

5. An arrangement according to claim 1, wherein a key-operated switch is provided at the rear end of the housing tube or cap, whereby the irradiation device can be switched on or off.

6. An arrangement according to claim 1, wherein the applicators are designed as one-time optics for a single use.

7. An arrangement according to claim 1, wherein the housing tube comprises an operation display.

8. An arrangement according to claim 1, wherein a protective film is provided in the housing tube in the beam path in front of the light source.

9. An arrangement according to claim 1, wherein the second connector body is designed as a plug or screw fastener having a depth stop.

10. An arrangement according to claim 1, wherein the light guide of the applicator is guided through the second connector body, with a distal end of the light guide protruding from the second connector body by a predetermined length when a connection is established with the irradiation device, so that the applicator engages in the head part.

11. An arrangement according to claim 2, wherein the wavelength of the laser diode is 660 nm.

12. An arrangement for reducing microorganisms, comprising:
- an irradiation device, which comprises a light source and a first connector body;
- a rotationally symmetric locking body having a first recess within which is positioned the light source, having a second recess within which is positioned a locking disk, and having a wall separating the light source and the locking disk, the wall having an opening through which light from the light source passes; and
- a one-time optics applicator in sterile condition and packaged for single use;
- wherein the locking disk is eccentrically positioned within the second recess by a wire spring to block light from exiting the opening;
- wherein the wire spring is mounted within a groove of the locking member in the second recess;
- wherein the locking disk has a conical surface with an opening at an apex of the conical surface;
- wherein the applicator comprises a light guide surrounded by a protective jacket and a second connector body, by means of which the applicator is detachably connected to the irradiation device via the first connector body thereof;
- wherein the first connector body and the second connector body correspond to each other and interlock with one another in such a way that the light of the light source can be irradiated through the light guide to a therapy site, onto which a light-activatable substance has been applied for therapeutic purposes;
- wherein upon insertion of said applicator the light guide is guided by the conical surface into the opening at the apex biasing the locking disk into an alignment of the wall opening and the locking disk opening;
- wherein for therapy of a region of the oral cavity, the light guide has a numerical aperture greater than 0.5 and one end free of the protective jacket, wherein the light beam emanating from the light guide opens up significantly, the dimensions of the applicator are specified so that it can be introduced into the oral cavity without difficulty and configured as a pocket probe having a pointed conical tip or as a flat probe;
- wherein the irradiation device comprises a housing tube and a head part situated at the front end thereof, which is configured as the first connector body;
- wherein the light source and an electronic circuit board having an externally actuatable button are located in the front part of the housing tube; and
- wherein batteries or rechargeable batteries for supplying the electronic units for the light source with power are further provided in the housing tube, with a cap being detachably connected to the rear end of the housing tube via a threaded joint.

13. An arrangement according to claim 12, wherein the light guide is bent.

14. An arrangement according to claim 12, wherein the light guide is straight.

15. An arrangement according to claim 12, wherein the one-time optics applicator in sterile condition and packaged for single use is a first applicator having a bent light guide, and further comprising a second applicator having a straight light guide.

* * * * *